US005665737A

United States Patent [19]
Cavalla et al.

[11] Patent Number: 5,665,737
[45] Date of Patent: Sep. 9, 1997

[54] SUBSTITUTED BENZOXAZOLES

[75] Inventors: John David Cavalla, Cambridge, England; Lloyd J. Dolby, Eugene, Oreg.; Peter Hofer, Liestal, Switzerland; Mark Chasin, Manalapan, N.J.

[73] Assignee: Euro-Celtique, S.A., Luxembourg, Luxembourg

[21] Appl. No.: 321,730

[22] Filed: Oct. 12, 1994

[51] Int. Cl.$^6$ ..................................................... A61K 31/42
[52] U.S. Cl. ..................... 514/338; 514/365; 514/367; 514/375; 548/179; 548/217; 548/205
[58] Field of Search .............................. 514/338; 546/270, 546/270.1, 271.7

[56] References Cited

U.S. PATENT DOCUMENTS

| | | | |
|---|---|---|---|
| 3,136,771 | 6/1964 | Leichti et al. | 546/270 |
| 3,494,919 | 2/1970 | Collins et al. | 548/217 |
| 3,541,100 | 11/1970 | Ramirez . | |
| 3,574,218 | 4/1971 | Hideg et al. | 548/217 |
| 3,674,781 | 7/1972 | Schinzel et al. | 548/217 |
| 3,706,834 | 12/1972 | Schellenbaum et al. | 514/375 |
| 4,020,165 | 4/1977 | Hubbard | 514/367 |
| 4,025,636 | 5/1977 | Dunwell et al. | 548/224 |
| 4,025,637 | 5/1977 | Dunwell et al. | 548/224 |
| 4,167,628 | 9/1979 | Kornawy et al. | 548/224 |
| 4,416,892 | 11/1983 | Dawson | 514/375 |
| 4,652,654 | 3/1987 | Verga et al. | 548/224 |
| 4,831,152 | 5/1989 | Itoh et al. | 548/224 |
| 4,910,211 | 3/1990 | Imamura | 514/367 |
| 5,190,942 | 3/1993 | Poss | 548/224 |
| 5,206,255 | 4/1993 | Ubasawa et al. | 514/375 |
| 5,264,589 | 11/1993 | Corey | 548/51 |
| 5,322,847 | 6/1994 | Marfat et al. | 514/303 |
| 5,451,596 | 9/1995 | Ullrich | 514/575 |
| 5,496,853 | 3/1996 | Shiota et al. | 514/375 |

FOREIGN PATENT DOCUMENTS

| | | | |
|---|---|---|---|
| 0178413 | 4/1986 | European Pat. Off. | C07D 235/18 |
| 0470805 | 2/1992 | European Pat. Off. | C07C 271/60 |
| 0497564 | 8/1992 | European Pat. Off. | C07C 235/36 |
| 0511865 | 11/1992 | European Pat. Off. | C07D 231/08 |
| 1498705 | 1/1978 | United Kingdom | A61K 31/40 |
| WO9219594 | 11/1992 | WIPO | C07D 207/26 |
| WO9307111 | 4/1993 | WIPO | C07C 49/753 |
| WO9314082 | 7/1993 | WIPO | C07D 401/04 |
| WO9315044 | 8/1993 | WIPO | C07C 237/22 |
| WO9315045 | 8/1993 | WIPO | C07C 237/22 |

OTHER PUBLICATIONS

Isomura et al. Chem. Abstr. vol. 100 Abstract 103220 (1984).

"Differential modulation of tissue function and therapeutic potential of selective inhibitors of cyclic nucleotide phosphodiesterase isoenzymes", C. David Nicholson, R. A. John Challiss and Mohammed Shahid, 1991, Elsevier Science Publishers Ltd. (UK), TIPS 12:19–27.

"Phosphodiesterase inhibitors: new opportunities for the treatment of asthma", Theodore J. Torphy, Bradley J. Undem, Thorax 1991; 46:512–523.

"Novel phosphodiesterase inhibitors for the therapy of asthma", Theodore J. Torphy, George P. Livi and Siegfried B. Christensen, DN&P 6(4), May 1993 203–214.

"Assay of cyclic nucleotide phosphodiesterase and resolution of multiple molecular forms of the enzyme", W. Joseph Thompson, Wesley L. Terasaki, Paul M. Epstein, Samuel J. Strada, Advances in Cyclic Nucleotide Research, vol. 10, 1979, 69–92.

"Identification, characterization and functional role of phosphodiesterase isozymes in human airway smooth muscle", Theodore J. Torphy, Bradley J. Undem, Lenora B. Cieslinski, Mark A. Luttmann, Martin L. Reeves and Douglas W. P. Hay, The Journal of Pharmacology and Experimental Therapeutics, 1993, vol. 265, No. 3, 1213–1223.

"The PDE IV family of calcium–independent phosphodiesterase enzymes", John A. Lowe III and John B. Cheng, Drugs of the Future 1992, 17(9): 799–807.

*Primary Examiner*—Donald G. Daus
*Attorney, Agent, or Firm*—Steinberg, Raskin & Davidson, P.C.

[57] ABSTRACT

Novel compounds which are effective PDE IV inhibitors are disclosed. The compounds possess improved PDE IV inhibition as compared to theophylline or rolipram, with improved selectivity with regard to, e.g., PDE III inhibition.

24 Claims, No Drawings

SUBSTITUTED BENZOXAZOLES

BACKGROUND OF THE INVENTION

Asthma is a complex disease involving the concerted actions of multiple inflammatory and immune cells, spasmogens, inflammatory mediators, cytokines and growth factors. In recent practice there have been four major classes of compounds used in the treatment of asthma, namely bronchodilators (e.g., β-adrenoceptor agonists), anti-inflammatory agents (e.g., corticosteroids), prophylactic anti-allergic agents (e.g., cromolyn sodium) and xanthines (e.g., theophylline) which appear to possess both bronchodilating and anti-inflammatory activity.

Theophylline has been a preferred drug of first choice in the treatment of asthma. Although it has been touted for its direct bronchodilatory action, theophylline's therapeutic value is now believed to also stem from anti-inflammatory activity. Its mechanism of action remains unclear. However, it is believed that several of its cellular activities are important in its activity as an anti-asthmatic, including cyclic nucleotide phosphodiesterase inhibition, adenosine receptor antagonism, stimulation of catecholamine release, and its ability to increase the number and activity of suppressor T-lymphocytes. While all of these actually may contribute to its activity, only PDE inhibition may account for both the anti-inflammatory and bronchodilatory components. However, theophylline is known to have a narrow therapeutic index, and a wide range of untoward side effects which are considered problematic.

Of the activities mentioned above, theophylline's activity in inhibiting cyclic nucleotide phosphodiesterase has received considerable attention recently. Cyclic nucleotide phosphodiesterases (PDEs) have received considerable attention as molecular targets for anti-asthmatic agents. Cyclic 3',5'-adenosine monophosphate (cAMP) and cyclic 3',5'-guanosine monophosphate (cGMP) are known second messengers that mediate the functional responses of cells to a multitude of hormones, neurotransmitters and autocoids. At least two therapeutically important effects could result from phosphodiesterase inhibition, and the consequent rise in intracellular adenosine 3',5'-monophosphate (cAMP) or guanosine 3',5'-monophosphate (cGMP) in key cells in the pathophysiology of asthma. These are smooth muscle relaxation (resulting in bronchodilation) and anti-inflammatory activity.

It has become known that there are multiple, distinct PDE isoenzymes which differ in their cellular distribution. A variety of inhibitors possessing a marked degree of selectivity for one isoenzyme or the other have been synthesized.

The structure-activity relationships (SAR) of isozyme-selective inhibitors has been discussed in detail, e.g., in the article of Theodore J. Torphy, et al., "Novel Phosphodiesterase Inhibitors For The Therapy Of Asthma", Drug News & Prospectives, 6(4) May 1993, pages 203–214. The PDE enzymes can be grouped into five families according to their specificity toward hydrolysis of cAMP or cGMP, their sensitivity to regulation by calcium, calmodulin or cGMP, and their selective inhibition by various compounds. PDE I is stimulated by $Ca^{2+}$/calmodulin. PDE II is cGMP-stimulated, and is found in the heart and adrenals. PDE III is cGMP-inhibited, and inhibition of this enzyme creates positive inotropic activity. PDE IV is cAMP specific, and its inhibition causes airway relaxation, anti-inflammatory and antidepressant activity. PDE V appears to be important in regulating cGMP content in vascular smooth muscle, and therefore PDE V inhibitors may have cardiovascular activity.

While there are compounds derived from numerous structure activity relationship studies which provide PDE III inhibition, the number of structural classes of PDE IV inhibitors is relatively limited. Analogues of rolipram, which has the following structural formula:

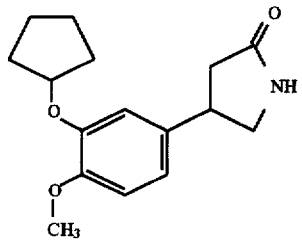

and of Ro-20-1724, which has the following structural formula:

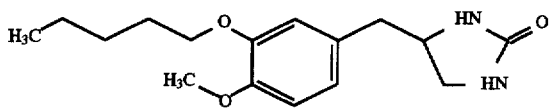

have been studied.

Rolipram, which was initially studied because of its activity as an antidepressant has been shown to selectively inhibit the PDE IV enzyme and this compound has since become a standard agent in the classification of PDE enzyme subtypes. There appears to be considerable therapeutic potential for PDE IV inhibitors. Besides initial work suggesting an anti-depressive action, rolipram has been investigated for its anti-inflammatory effects, particularly in asthma. In-vitro, rolipram, Ro-20-1724 and other PDE IV inhibitors have been shown to inhibit (1) mediator synthesis/release in mast cells, basophils, monocytes and eosinophils; (2) respiratory burst, chemotaxis and degranulation in neutrophils and eosinophils; and (3) mitogen-dependent growth and differentiation in lymphocytes (The PDE IV Family Of Calcium-Phosphodiesterases Enzymes, John A. Lowe, III, et al., Drugs of the Future 1992, 17(9):799–807).

PDE IV is present in all the major inflammatory cells in asthma including eosinophils, neutrophils, T-lymphocytes, macrophages and endothelial cells. Its inhibition causes down regulation of cellular activation and relaxes smooth muscle cells in the trachea and bronchus. On the other hand, inhibition of PDE III, which is present in myocardium, causes an increase in both the force and rate of cardiac contractility. These are undesirable side effects for an anti-inflammatory agent. Theophylline, a non-selective PDE inhibitor, inhibits both PDE III and PDE IV, resulting in both desirable anti-asthmatic effects and undesirable cardiovascular stimulation. With this well-known distinction between PDE isozymes, the opportunity for concomitant anti-inflammation and bronchodilation without many of the side effects associated with theophylline therapy is apparent. The increased incidence of morbidity and mortality due to asthma in many Western countries over the last decade has focused the clinical emphasis on the inflammatory nature of this disease and the benefit of inhaled steroids. Development of an agent that possesses both bronchodilatory and anti-inflammatory properties would be most advantageous.

It appears that selective PDE IV inhibitors should be more effective with fewer side effects than theophylline. Clinical support has been shown for this hypothesis.

Attempts have therefore been made to find new compounds having more selective and improved PDE IV inhibition.

OBJECTS AND SUMMARY OF THE INVENTION

It is accordingly a primary object of the present invention to provide new compounds which are effective PDE IV inhibitors.

It is another object of the present invention to provide new compounds which act as effective PDE IV inhibitors with lower PDE III inhibition.

It is a further object of the present invention to provide new compounds which have a superior PDE IV inhibitory effect as compared to rolipram or other known compounds.

It is a further object of the present invention to provide new compounds which have a substantially equal or superior PDE IV inhibitory effect as compared to known chemical compounds, and which exhibit surprisingly greater selectivity with regard to their inhibitory effects.

It is another object of the present invention to provide a method of treating a patient requiring PDE IV inhibition.

It is another object of the present invention to provide new compounds for treating disease states associated with abnormally high physiological levels of cytokines, including tumor necrosis factor.

It is another object of the present invention to provide a method of synthesizing the new compounds of this invention.

It is another object of the present invention to provide a method for treating a mammal suffering from a disease state selected from the group consisting of asthma, allergies, inflammation, depression, dementia, a disease caused by Human Immunodeficiency Virus and disease states associated with abnormally high physiological levels of cytokines.

With the above and other objects in view, the present invention mainly comprises a compound of the formula:

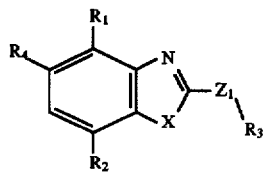

wherein:

X is O or S;

$R_1$ and $R_2$ are independently selected from hydrogen, halogen, hydroxy, nitro, $QZ_2$, $OQZ_2$, $OCOQZ_2$, $NHQZ_2$ or $NHCOQZ_2$ wherein:

Q is a saturated or unsaturated straight-chain or branched alkylene, alkenylene or alkynylene group containing from 1 to 12 carbon atoms;

$Z_2$ is hydrogen, hydroxy, alkoxy, acyloxy, oxo, 1-oxoalkyl, carboxy, carbalkyloxy, (alkyl)carbamyl, hydroxycarbamyl, (alkyl)carbamido, hydroxycarbamido, (acyl)oximido, carbamyloximido, N-hydroxy-acylamino, aryl or a heteroaryl ring containing one or more of members of the group selected from nitrogen, oxygen and sulfur; said aryl or heteroaryl ring being unsubstituted or further substituted with one or more halogen atoms, alkyl groups, OH, OQH, $NO_2$, $NH_2$, $CO_2QH$, $CON(QH)_2$, $OCOQH$, and $OCON(QH)_2$;

$R_3$ is an unsubstituted aryl or aryl substituted with 1-3 members of the group consisting of OH, O-alkyl, O(CO)alkyl, O-cycloalkyl, halogen, $NH_2$, $NO_2$, HO-alkyl, $R_5$ or $R_6$, wherein $R_5$ and $R_6$ are substituted alkyls as defined in detail below;

$Z_1$ is a linkage selected from a bond, $-CH_2-$, $-CH=CH-$, $-CH_2CH_2-$, $-CH(CH_3)-$ and $-C(CH_3)_2-$; except that $Z_1R_3$ is not 3,5-di-t-butyl-4-hydroxy-phenyl; and $R_4$ is hydrogen or a halogen.

The term "lower alkyl" is defined for purposes of the present invention as straight or branched chain radicals having from 1 to 3 carbon atoms.

DETAILED DESCRIPTION

The compounds of the present invention, as demonstrated in the appended examples, are effective in the mediation or inhibition of PDE IV in humans and other mammals. Further, these compounds are selective PDE IV inhibitors which possess both bronchodilatory and anti-inflammatory properties substantially without undesirable cardiovascular stimulation caused by PDE III inhibition. Many of these compounds have a substantially equal or superior PDE IV inhibitory effect as compared to theophylline.

The present invention is further related to a method for the treatment of allergic and inflammatory disease which comprises administering to a mammal in need thereof an effective amount of the compounds of the present invention.

The present invention is also related to a method for the mediation or inhibition of the enzymatic or catalytic activity of PDE IV activity in mammals, particularly humans, which comprises administering an effective amount of the above-described compounds of the invention to a mammal in need of PDE IV inhibition.

The compounds of the present invention may find use in the treatment of other disease states in humans and other mammals, such as in the treatment of disease states associated with a physiologically detrimental excess of tumor necrosis factor (TNF). TNF activates monocytes, macrophages and T-lymphocytes. This activation has been implicated in the progression of Human Immunodeficiency Virus (HIV) infection and other disease states related to the production of TNF and other cytokines modulated by TNF.

In certain preferred embodiments, the compounds of the present invention comprise the formula:

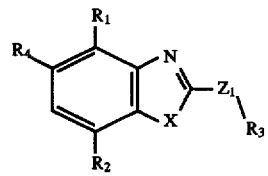

wherein:

X is O or S; and preferably O;

$R_1$ and $R_2$ are independently selected from hydrogen, halogen, hydroxy, nitro, $QZ_2$, $OQZ_2$, $OCOQZ_2$, $NHQZ_2$ or $NHCOQZ_2$ wherein:

Q is a saturated or unsaturated straight-chain or branched alkylene, alkenylene or alkynylene group containing from 1 to 12 carbon atoms;

$Z_2$ is hydrogen, hydroxy, alkoxy, acyloxy, oxo, 1-oxoalkyl, carboxy, carbalkyloxy, (alkyl)carbamyl, hydroxycarbamyl, (alkyl)carbamido, hydroxycarbamido, (acyl)oximido, carbamyloximido, N-hydroxy-acylamino, aryl or a heteraryl ring containing one or more of members of the group selected from nitrogen, oxygen and sulfur; said aryl or heteroaryl ring being unsubstituted or further substituted with one or more halogen atoms, alkyl groups, OH, OQH, NO$_2$, NH$_2$, CO$_2$QH, CON(QH)$_2$, OCOQH, and OCON(QH)$_2$;

except that R$_1$ and R$_2$ are not both hydrogen;

R$_3$ is an unsubstituted aryl or aryl substituted with 1–3 members of the group consisting of OH, O-alkyl, O(CO)alkyl, O-cycloalkyl, halogen, NH$_2$, NO$_2$, HO-alkyl, R$_5$ or R$_6$;

Z$_1$ is a linkage selected from a bond, —CH$_2$—, —CH=CH—, —CH$_2$CH$_2$—, —CH(CH$_3$)— and —C(CH$_3$)$_2$—;

except that Z$_1$R$_3$ is not 3,5,-di-t-butyl-4-hydroxy-phenyl;

R$_4$ is hydrogen or a halogen;

R$_5$ is hydrogen or branched or straight chain alkyl group of 1–12 carbon atoms, preferably lower alkyl, most preferably methyl or ethyl; and R$_6$ is an alkyl group of 1–12 carbon atoms, which may be substituted by one or more halogens, or cycloalkyl of 3–6 carbon atoms, preferably cyclopentyl which may be substituted by R$_7$ as shown in the following structural formula:

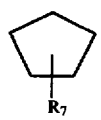

wherein R$_7$ is hydrogen or a saturated or unsaturated straight-chain lower alkyl group containing from about 1 to about 6 carbon atoms, unsubstituted or substituted with one or more halogen atoms, hydroxyl groups, cyano groups, nitro groups, carboxyl groups, alkoxy groups, alkoxycarbonyl, carboxamido or substituted or unsubstituted amino groups.

In certain preferred embodiments, R$_4$ is a halogen, such as chlorine; one of R$_1$ or R$_2$ is hydrogen and X is oxygen or sulfur and preferably oxygen.

In further preferred embodiments, Z$_1$ is a linkage selected from the group consisting of —CH$_2$—, —CH$_2$CH$_2$— and —CH=CH—.

In those aspects of the invention where one or both of R$_1$ and R$_2$ are QZ$_2$, Q is preferably an alkenylene or alkynylene group. Suitable alkenylene groups include, for example,— CH=CH—, and —CH$_2$—CH=CH—; suitable alkynyl groups include —C≡C—, and —C≡C—CH$_2$—.

Still further aspects of the invention include Q as an alkylene group. A non-limiting list of suitable groups include —CH$_2$CH$_2$—, —CH$_2$CH$_2$CH$_2$—.

Within this aspect of the invention, Z$_2$, where included, is preferably a 2-pyridine or 2-thiazole group.

R$_3$ can include an unsubstituted or substituted phenyl group such as phenyl, chlorophenyls, fluorophenyls, bichloro and bifluorophenyls, chloro-fluorophenyls and the like. Other aspects of the invention include R$_3$ groups such as 3,5-di-t-butyl-4-hydroxyphenyl; 3,5-di-t-butyl-4-acetoxyphenyl; 3,4-dimethoxyphenyl and 3-cyclopentyloxy-4-methoxyphenyl.

In another aspect of the invention, when X is O or S, preferably O and Z$_1$ is —CH$_2$—, R$_3$ is

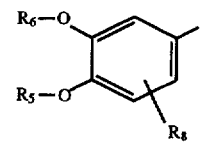

wherein

R$_5$ is hydrogen or branched or straight chain alkyl group of 1–12 carbon atoms, preferably lower alkyl, most preferably methyl or ethyl, and R$_6$ is an alkyl group of 1–12 carbon atoms, which may be substituted by one or more halogens, or cycloalkyl of 3–6 carbon atoms, preferably cyclopentyl which may be substituted by R$_7$ as shown in the following structural formula:

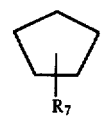

wherein R$_7$ is hydrogen or a saturated or unsaturated straight-chain lower alkyl group containing from about 1 to about 6 carbon atoms, unsubstituted or substituted with one or more halogen atoms, hydroxyl groups, cyano groups, nitro groups, carboxyl groups, alkoxy groups, alkoxycarbonyl, carboxamido or substituted or unsubstituted amino groups;

R$_8$ is hydrogen, lower alkyl or halogen.

Certain preferred compounds of the present invention include:

(I) 7-allyl-5-chloro-2-(3-cyclopentyloxy-4-methoxybenzyl)-benzoxazole;

(II) 5-chloro-2-(3,5-di-t-butyl-4-hydroxy-benzyl)-7-(2-(2-pyridyl)-ethynyl)-benzoxazole;

(III) 5-chloro-2-(3,5-di-t-butyl-4-hydroxy-benzyl)-7-(2-(2-thiazolyl)-ethynyl)-benzoxazole;

(IV) 7-bromo-5-chloro-2-(3-cyclopentyloxy-4-methoxy-benzyl)-benzoxazole;

(V) 7-bromo-5-chloro-2-(3,4-dimethoxy-benzyl)-benzoxazole;

(VI) 2-(3-cyclopentyloxy-4-methoxy-benzyl)-7-nitro-benzoxazole;

(VII) 2-(3-cyclopentyloxy-4-methoxy-benzyl)-4-hydroxy-benzoxazole; and (VIII) 4-acetoxy-2-(3-cyclopentyloxy-4-methoxy -benzyl)benzoxazole.

Description of the synthesis of these molecules is set forth in the Examples. The synthesis of other molecules not specifically shown in the examples but within the scope of the invention are carried out using those techniques shown with modifications which are known to those of ordinary skill in the art.

The compounds of the present invention have been found to be highly effective PDE IV inhibitors, the inhibition of which is in fact significantly and surprisingly greater than that of theophylline which exhibits 50% inhibition of PDE IV at around 350 µM. In addition, the concentration which yields 50% inhibition of PDE IV (IC$_{50}$) for the compound prepared in Example 1 is 0.6 µM, whereas the IC$_{50}$ for rolipram when run in the same assay was 2.8 µM. Historically, the IC$_{50}$ for rolipram is considered to be 3.5 µM. In any case, it is apparent that this inventive compound is several times as effective as a PDE IV inhibitor as compared to rolipram (or theophylline).

While the PDE III inhibition of an Example 1 compound is only 22% at 10 μM, it is clear that the compound of the invention is highly selective as a PDE IV inhibitor.

Accordingly, the compounds of the present invention can be administered to anyone requiring PDE IV inhibition. Administration may be orally, topically, by suppository, inhalation or insufflation, or parenterally.

The present invention also encompasses, where appropriate, all pharmaceutically acceptable salts of the foregoing compounds. One skilled in the art will recognize that acid addition salts of the presently claimed compounds may be prepared by reaction of the compounds with the appropriate acid via a variety of known methods. Alternatively, alkali and alkaline earth metal salts are prepared by reaction of the compounds of the invention with the appropriate base via a variety of known methods.

Various oral dosage forms can be used, including such solid forms as tablets, gelcaps, capsules, caplets, granules, lozenges and bulk powders and liquid forms such as emulsions, solution and suspensions. The compounds of the present invention can be administered alone or can be combined with various pharmaceutically acceptable carriers and excipients known to those skilled in the art, including but not limited to diluents, suspending agents, solubilizers, binders, disintegrants, preservatives, coloring agents, lubricants and the like.

When the compounds of the present invention are incorporated into oral tablets, such tablets can be compressed, tablet triturates, enteric-coated, sugar-coated, film-coated, multiply compressed or multiply layered. Liquid oral dosage forms include aqueous and nonaqueous solutions, emulsions, suspensions, and solutions and/or suspensions reconstituted from non-effervescent granules, containing suitable solvents, preservatives, emulsifying agents, suspending agents, diluents, sweeteners, coloring agents, and flavorings agents. When the compounds of the present invention are to be injected parenterally, they may be, e.g., in the form of an isotonic sterile solution. Alternatively, when the compounds of the present invention are to be inhaled, they may be formulated into a dry aerosol or may be formulated into an aqueous or partially aqueous solution.

In addition, when the compounds of the present invention are incorporated into oral dosage forms, it is contemplated that such dosage forms may provide an immediate release of the compound in the gastrointestinal tract, or alternatively may provide a controlled and/or sustained release through the gastrointestinal tract. A wide variety of controlled and/or sustained release formulations are well known to those skilled in the art, and are contemplated for use in connection with the formulations of the present invention. The controlled and/or sustained release may be provided by, e.g., a coating on the oral dosage form or by incorporating the compound(s) of the invention into a controlled and/or sustained release matrix.

Specific examples of pharmaceutically acceptable carriers and excipients that may be used for formulate oral dosage forms, are described in the Handbook of Pharmaceutical Excipients, American Pharmaceutical Association (1986), incorporated by reference herein. Techniques and compositions for making solid oral dosage forms are described in Pharmaceutical Dosage Forms: Tablets (Lieberman, Lachman and Schwartz, editors) 2nd edition, published by Marcel Dekker, Inc., incorporated by reference herein. Techniques and compositions for making tablets (compressed and molded), capsules (hard and soft gelatin) and pills are also described in Remington's Pharmaceutical Sciences (Arthur Osol, editor), 1553–1593 (1980), incorporated herein by reference. Techniques and composition for making liquid oral dosage forms are described in Pharmaceutical Dosage Forms: Disperse Systems, (Lieberman, Rieger and Banker, editors) published by Marcel Dekker, Inc., incorporated herein by reference.

When the compounds of the present invention are incorporated for parenteral administration by injection (e.g., continuous infusion or bolus injection), the formulation for parenteral administration may be in the form of suspensions, solutions, emulsions in oily or aqueous vehicles, and such formulations may further comprise pharmaceutically necessary additives such as stabilizing agents, suspending agents, dispersing agents, and the like. The compounds of the invention may also be in the form of a powder for reconstitution as an injectable formulation.

The dose of the compounds of the present invention is dependent upon the affliction to be treated, the severity of the symptoms, the route of administration, the frequency of the dosage interval, the presence of any deleterious side-effects, and the particular compound utilized, among other things.

The PDE IV inhibitory compounds of the present invention may be examined for their PDE IV inhibitory effects via the techniques set forth in the following examples, wherein the ability of the compounds to inhibit PDE IV isolated from bovine tracheal smooth muscle is set forth.

DESCRIPTION OF THE PREFERRED EMBODIMENTS

The following examples illustrate various aspects of the present invention, and are not to be construed to limit the claims in any manner whatsoever.

EXAMPLE 1

7-allyl-5-chloro-2-(3-cyclopentyloxy-4-methoxybenzyl)-benzoxazole a) 3-cyclopentyloxy-4-methoxybenzaldehyde A mixture of 3-hydroxy-4-methoxybenzaldehyde (40 g, 0.26 mol), potassium carbonate (40 g, 0.29 mol) and bromocyclopentane (32 ml, 0.31 mol) in dimethylformamide (0.25 l) was heated under an argon atmosphere at 100° C. After 4 hours, additional bromocyclopentane (8.5 ml, 0.08 mol) was added and heating was continued for 4 hours. The mixture was allowed to cool and was filtered. The filtrate was concentrated under reduced pressure and the residue was partitioned between ether and aqueous sodium bicarbonate. The organic extract was washed with aqueous sodium carbonate and was dried (potassium carbonate). The solvent was removed in-vacuo and the residue was purified by flash chromatography, eluting with 2:1 [may also be distilled at ~0.02 mm Hg] hexanes/ether to provide a pale yellow oil (52 g, 89%).

Analysis Calc. for $C_{13}H_{16}O_3$; C 70.89, H 7.32; found: C 70.71, H 7.33 b) 3-cyclopentyloxy-4-methoxybenzyl alcohol

A solution of 3-cyclopentyloxy-4-methoxybenzaldehyde (38 g 0.17 mol) in 40 ml of ethanol and sodium borohydride (1.63 g, 0.043 mol) was stirred for 2 hours at room temperature at which time the reaction was complete by TLC. The reaction was diluted with water and extracted with ethyl acetate. Evaporation of the ethyl acetate afforded 3-cyclopentyloxy-4-methoxybenzyl alcohol (37 g, 98%) suitable for the next step.

c) 3-cyclopentyloxy-4-methoxybenzyl chloride

A solution of 3-cyclopentyloxy-4-methoxybenzyl alcohol (112 g, 0.50 mol) prepared as described above, in 1 liter of methylene chloride was stirred at room temperature with concentrated HCl (110 ml, 1.2 mol) for 3 hours at which time the reaction was done by TLC. The layers were separated and the methylene chloride solution was washed twice with water and evaporated under reduced pressure to give 3-cyclopentyloxy-4-methoxybenzyl chloride (119 g, 100%).

d) 3-cyclopentyloxy-4-methoxyphenylacetonitrile

A mixture of 3-cyclopentyloxy-4-methoxybenzyl chloride (119 g, 0.49 mol), 120 ml of methylene chloride, KCN (70.7 g, 1.09 mol), benzyltriethylammonium chloride (35 g, 0.015 mol) and water e120 ml) was stirred vigorously at room temperature for 48 hours when the reaction was complete by HPLC. The reaction mixture was diluted with methylene chloride and the layers were separated. The methylene chloride solution was extracted several times with water and evaporated to afford 3-cyclopentyloxy-4-methoxyphenylacetonitrile (109 g, 95%) of sufficient purity to be used in the subsequent transformation.

e) 3-cyclopentyloxy-4-methoxyphenylacetic acid

A solution of 3-cyclopentyloxy-4-methoxyphenylacetonitrile (109 g, 0.43 mol) in 1330 ml of ethanol and NaOH (51 g, 1.3 mol) was heated under reflux for 48 hours. Ethanol (500 ml) was distilled from the reaction mixture and the residue was diluted with water and stirred with Norit A (11 g) for 2 min. The mixture was filtered through a pad of celite and acidified to pH 1 with concentrated HCl. Extraction of the mixture with ether afforded 120 g of crude 3-cyclopentyloxy-4-methoxyphenylacetic acid after evaporation of the ether at reduced pressure. The crude acid was dissolved in warm toluene (400 ml) and stirred for 1 hour with 10.5 g of Norit A. The charcoal was filtered and the toluene solution was diluted with heptane (400 ml). Filtration of the cooled solution afforded 72 g (67%) of pure 3-cyclopentyloxy-4-methoxyphenylacetic acid, mp 79°–80° C.

f) N-(3-cyclopentyloxy-4-methoxyphenylacetyl)-2-hydroxy-5-chloroaniline

To a stirred slurry of 1,1'-carbonyldiimidazole (7.1 g, 0.044 mol) in 40 ml of methylene chloride was added dropwise a solution of 3-cyclopentyloxy-4-methoxyphenylacetic acid (10 g, 0.040 mol) in 20 ml of methylene chloride. After stirring for 2 hours the resulting solution was added to a solution of 2-hydroxy-5-chloroaniline (6.0 g, 0.042 mol) in methylene chloride (75 ml). After stirring overnight, water was added and stirring was continued. The layers were separated and the methylene chloride layer was washed with 100 ml portion of water, dilute aqueous HCl, and water. Evaporation of the methylene chloride afforded the solid amide which was triturated with methanol (20 ml) and filtered to give 10.7 g (71%) of N-(3-cyclopentyloxy-4-methoxyphenylacetyl)-2-hydroxy-5-chloroaniline, mp 151°–152° C.

g) N-(3-cyclopentyloxy-4-methoxyphenylacetyl)-2-allyloxy-5-chloroaniline

To a stirred solution of N-(3-cyclopentyloxy-4-methoxyphenylacetyl)-2-hydroxy-5-chloroaniline (78g, 0.21 mol) in ethanol (600 ml) and 1N NaOH in methanol (213 ml) was added allyl chloride (23.3 g, 0.31 mol). The mixture was heated under reflux for 8 hours, after which it was diluted with water and extracted twice with ethyl acetate. Evaporation of the ethyl acetate and crystallization of the residue from methanol gave 56.4 g (65%) of the title compound, mp 75°–76.5° C.

h) 7-allyl-5-chloro-2-(3-cyclopentyloxy-4-methoxybenzyl)-benzoxazole

A solution of N-(3-cyclopentyloxy-4-methoxyphenylacetyl)-2-allyloxy-5-chloroaniline (38.1 g, 0.092 mol) in 200 ml of diphenyl ether was heated under nitrogen at 180° for 8 hours. Protracted heating resulted in reduced yields. The reaction mixture was diluted with 500 ml of petroleum ether, applied to a column packed with 500 g of flash chromatography silica gel and eluted with petroleum ether followed by methylene chloride. Fractions of 800 ml were collected. The material from fractions 9–14 weighed 30 g (80% of theoretical). This material was recrystallized from hexane to give 19 g (52%) of the title compound, mp 43°–44° C., which was greater than 98.3% pure by HPLC.

HPLC conditions

Reactions were monitored by HPLC using an Alltech Alltima column, C 18, 5 microns, 250×4.6 mm. Solvent: methanol/water (85:15), 1 ml/min at 254 nm. Retention time: 21 min.

EXAMPLE 2

5-chloro-2-(3,5-di-t-butyl-4-hydroxy-benzyl)-7-(2-(2-pyridyl)-ethynyl)-benzoxazole a) 2-bromo-4-chloro-6-nitro-phenol A solution of 2-bromo-4-chloro-phenol (99.24 g, 480 mM) in acetic acid (110 ml) and acetic anhydride (125 ml) was cooled to −10° C. Within 1 hour a solution containing 100% nitric acid (33 ml) and acetic acid (40 ml) was added between −10° and −5° C., with stirring. The mixture was stirred for an additional 1.5 hours at 0°–5° C., then the suspension poured onto 300 g of ice in 700 ml of water and stirred for a further 0.5 hour. The solid was collected, washed, and dried to give 97.12 g (80.1%) of the title compound (mp 121°–2° C.).

b) 6-amino-2-bromo-4-chloro-phenol

A solution of 2-bromo-4-chloro-6-nitro-phenol (16.27 g, 64.4 mM) in ethyl acetate (160 ml) was hydrogenated, at room temperature, with Raney-nickel (6 g). After hydrogen uptake (approx. 4.8 1) was complete, the nickel was removed by filtration and the filtrate evaporated in-vacuo to give 14.19 g (99.0%) of the title compound which was suitable for the next step.

c) N,O-di-(3,5-di-t-butyl-4-hydroxy-phenylacetyl)-6-amino-2-bromo-4-chloro-phenol Water (173 ml) and sodium carbonate (33.24 g, 310 mM) were added to a stirred ethereal solution (123 ml) of 6-amino-2-bromo-4-chloro-phenol (17.45 g, 78.4 mM). After 15 minutes 3,5-di-t-butyl-4-hydroxy-phenylacetyl chloride (47.60 g, 93.1%, 156.8 mM) (prepared with thionyl chloride from the corresponding acid), was added at −5° to 0° C. and stirring continued for a further 1.5 hours without cooling. The aqueous phase was adjusted to pH 8 and the layers separated. The organics were washed with 1N HCl (100 ml) and saturated aqueous sodium bicarbonate solution (100 ml), dried ($Na_2SO_4$) and evaporated in-vacuo to give 58.1 g (103.6%) of the title compound which was suitable for the next step.

d) 2-bromo-4-chloro-6-(3,5-di-t-butyl-4-hydroxy-phenylacetyl-amino)-phenol

A solution of N,O-Di-(3,5-di-t-butyl-4-hydroxy-phenylacetyl)-6-amino-2-bromo-4-chloro-phenol (58.1 g, 89.8 mM) in methanol (400 ml) and potassium carbonate (24.78 g, 180 mM) was stirred at room temperature for 10 minutes. The methanol was removed in-vacuo, the residue treated with 2N HCl (180 ml, 360 mM), and extracted with ethyl acetate (300 ml). The organics were dried ($Na_2SO_4$), evaporated in-vacuo, and the residue suspended in petroleum ether. The precipitate was collected to give 37.44 g (88.9%) of the title compound which was suitable for the next step.

e) 7-bromo-5-chloro-2-(3,5-di-t-butyl-4-hydroxy-benzyl)-benzoxazole

A solution of 2-bromo-4-chloro-6-(3,5-di-t-butyl-4-hydroxy-phenylacetyl-amino)-phenol (35.67 g, 76.1 mM) and phosphorus oxychloride (41.8 ml, 457mM) in toluene was heated under reflux for 1 hour. Volatiles were removed in-vacuo and residual amounts of phosphorus oxychloride removed by azeotropic distillation with toluene (2×50 ml). The residue was taken up in acetone (50 ml) and ether (100 ml), and treated with water (100 ml) and saturated aqueous sodium bicarbonate solution (100 ml). The organic solvents were removed in-vacuo and the precipitate collected to give 33.36 g (93.6%) of crude benzoxazole. The crude benzoxazole was dissolved in dichloromethane (100 ml), filtered, and the filtrate diluted with methanol (100 ml). The dichloromethane was removed by distillation and the resulting crystals collected, washed, and dried in-vacuo to give 28.86 g (80.9%) of the title compound (mp 133°–6° C.).

f) 5-chloro-2-(3,5-di-t-butyl-4-hydroxy-benzyl)-7-ethynyl-benzoxazole

A suspension of 7-bromo-5-chloro-2-(3,5-di-t-butyl-4-hydroxy-benzyl)-benzoxazole (13.50 g, 30 mM), trimethylsilylacetylene (4.41 g, 6.36 ml, 45 mM), bis(triphenylphosphine) palladium (II) dichloride (105 mg, 150 uM) and copper (I) iodide (5.75 mg, 30uM) in triethylamine (60 ml) was heated at 90° C., under argon, for 3 hours. The mixture was cooled to room temperature, diluted with water (375 ml) and the excess triethylamine removed in-vacuo. The solid was removed by filtration and the filtrate evaporated in-vacuo to give 14.00 g (100%) of crude trimethylsilylacetylene derivative. A suspension of the crude trimethylsilylacetylene derivative (14 g) in methanol (140 ml) and potassium carbonate (6.20 g, 45 mM) was stirred at room temperature, under nitrogen, for 10 minutes; 2N HCl (45 ml, 90 mM) was added slowly and the formed suspension evaporated in-vacuo. The residue was taken up in dichloromethane (200 ml), the salt removed by filtration and the filtrate evaporated in-vacuo to give 12.21 g (102.8%) of crude 5-chloro-2-(3,5-di-t-butyl-4-hydroxy-benzyl)-7-ethynyl-benzoxazole. The crude ethynyl-benzoxazole was dissolved in dichloromethane (40 ml) and filtered through 60 g of silica gel. The product was recrystallised from methanol to give 8.10 g (68.2%) of the title compound (mp 152°–5° C.). From the filtrate a second crop of 1.31 g (11.0%) was also obtained.

Elemental analysis for $C_{24}H_{26}ClNO_2$ Calc. C 72.81 H 6.62 N 3.54 0 8.10 Found C 72.26 H 6.60 N 3.72 0 8.07 g) 5-chloro-2-(3,5-di-t-butyl-4-hydroxy-benzyl)-7-(2-(2-pyridyl)-ethynyl)-benzoxazole A suspension of 5-chloro-2-(3,5-di-t-butyl-4-hydroxy-benzyl)-7-ethynyl-benzoxazole (2.38 g, 6.0 mM), 2-bromo-pyridine (0.66 ml, 98%, 6.6 mM), bis(triphenylphosphine) palladium(II) dichloride (21.1 mg, 30 uM) and copper (I) iodide (1.2 mg, 6 uM) in triethylamine (12 ml) was heated at 90° C., under argon, for 1.5 hours. The triethylamine was removed in-vacuo and the residue dissolved in ether (100 ml). The organics were washed with water (50 ml), 1N HCl (100 ml) and saturated aqueous sodium hydrogen carbonate (100 ml), dried (Na₂SO₄) and evaporated in-vacuo to give 2.96 g (104.2%) of crude pyridylethynylbenzoxazole. The crude benzoxazole was purified by column chromatography (SiO₂; dichloromethane), and the product crystallized from methanol and suspended in hot water. The resulting crystals were collected, washed, and dried to give 1.49 g (52.5%) of the title compound (top 138°–9° C.).

Elemental analysis for $C_{29}H_{29}ClN_2O_2$ Calc. C 73.64 H 6.18 N 5.92 0 6.76 Found C 73.62 H 5.97 N 5.91 0 6.93

EXAMPLE 3

5-chloro-2-(3,5-di-t-butyl-4-hydroxy-benzyl)-7-(2-(2-thiazolyl)-ethynyl-benzoxazole A suspension of 5-chloro-2-(3,5-di-t-butyl-4-hydroxy-benzyl)-7-ethynyl-benzoxazole (2.38 g, 6.0 mM), 2-bromothiazole (1.13 ml, 95%, 12 mM), bistriphenylphosphine)palladium(II) dichloride (21.1 mg, 30 uM), copper (I) iodide (1.2 mg, 6 uM) in triethylamine (12 ml) was heated at 90° C., under argon, for 3 hours. The triethylamine was removed in-vacuo and the residue dissolved in ether (70 ml) and water (30 ml). The organics were washed with 1N HCl (30 ml) and saturated sodium hydrogen carbonate (30 ml), dried (Na₂SO₄) and evaporated in-vacuo to give 2.86 g (100%) of crude thiazolylethynylbenzoxazole, which was purified by flash chromatography (SiO₂; dichloromethane). The product was crystallized and recrystallized from methanol to give 1.43 g (50.4%) of the title compound (mp 137°–41° C.).

Elemental analysis for $C_{27}H_{27}ClN_2O_2S$ Calc. C 67.70 H 5.68 N 5.85 0 6.68 Found C 67.62 H 5.40 N 5.65 0 6.76

EXAMPLE 4

7-bromo-5-chloro-2-(3-cyclopentyloxy-4-methoxybenzyl)-benzoxazole (a) N,O-di(3-cyclopentyloxy-4-methoxy-phenylacetyl)-6-amino-2-bromo-4-chloro-phenol A solution of 48.7 g of 3-cyclopentyloxy-4-methoxyphenylacetyl chloride in 240 ml of ether was added, at 0°–5° C. within 10 min, to a two phase solution of 19.6 g of 2-amino-3-bromo-5-chlorophenol (freshly prepared) in 300 ml of ether and 60 ml water. After 1 hr at 15° C. the ether was removed in vacuo and the brownish solid collected, washed with water and dried to give 58.95 g of crude amide ester.

(b) 2-Bromo-4-chloro-6-(3-cyclopentyloxy-4-methoxy-phenyl-acetylamino)-phenol

A suspension of 58.7 g of N,O-di(3-cyclopentyloxy-4-methoxy-phenylacetyl)-6-amino-2-bromo-4-chloro-phenol in 200 ml of isopropanol was added at 10° C. to a two phase solution of 9.59 g of potassium hydroxide in 6.15 ml of water and 490 ml of isopropanol. After 15 min practically all the solid was dissolved. After 45 min 200 ml of water was added and the suspension brought to pH 7 with 85 ml of 1N HCl. The isopropanol was removed in vacuo and 50 ml of saturated sodium bicarbonate solution added to bring the pH to about 8. After 45 min the solid was collected, washed with bicarbonate and water until neutral, and dried to give 43.2 g of crude amide; the filtrate was acidified and 16.87 g of 3-cyclopentyloxy-4-methoxyphenylacetic acid recovered.

The crude amide was suspended in 200 ml of dichloromethane and the solid collected to give 31.30 g of purified amide.

(c) 7-bromo-5-chloro-2-(3-cyclopentyloxy-4-methoxybenzyl)-benzoxazole

A suspension of 32.9 g (72.4 mM) of the 2-Bromo-4-chloro-6-(3-cyclopentyloxy-4-methoxy-phenylacetylamino)-phenol in 400 ml of toluene and 39.7 ml (434 mM) of phosphorus oxychloride was refluxed for 1.5 hr. Some solid material was filtered off and the filtrate evaporated to dryness in vacuo. The honey-like residue was suspended in 200 ml of sodium bicarbonate solution for 1 hr. The solid was collected, washed and dried at 25° C. to give 22.53 g (71.2%) of crude benzoxazole.

The crude material was dissolved in 100 ml of dichloromethane and filtered through 60 g of silica gel. Crystallisation from methanol afforded 19.46 g (61.9%) of pure benzoxazole (mp 90°–1° C.).

EXAMPLE 5

7-bromo-5-chloro-2-(3,4-dimethoxybenzyl)benzoxazole

By using a similar procedure to Example 4 employing 3,4-dimethoxy-phenylacetyl chloride and 2-amino-3-bromo-5-chlorophenol the title compound was obtained (mp 123°–124° C.).

EXAMPLE 6

2-(3-cyclopentyloxy-4-methoxybenzyl)-7-nitrobenzoxazole (a) 2-amino-6-nitrophenol A suspension of 2,6-dinitrophenol (5 g), ammonia (3 ml) and ammonium chloride (14.30 g) in water (30 ml) was heated to 70° C. A solution of sodium sulphide nonahydrate (24.19 g) in water (23 ml) was added and the resulting mixture stirred at 70° C. for 2 hours. The reaction was cooled to room temperature, acidified (pH 3.2) with 2N HCl, and the brown precipitate isolated by filtration. The filtrate was extracted with chloroform (6×75 ml), the organic extracts combined with the precipitate, and evaporated in-vacuo to yield a dark brown solid. The solid was purified by flash chromatography (SiO2; dichloromethane) to yield the title compound (2.86 g, 68%) as a brown solid. $\delta_H$ (250 MHZ;$d_6$ DMSO), 6.75 (1H,td,ArH), 6.90 (2H,bs,ArNH$_2$), 6.92 (1H,m,ArH), 7.14 (1H,m,ArH).

(b) N-(2-hydroxy-3-nitrophenyl)-3-cyclopentyloxy-4-methoxy-phenylacetamide

A suspension of 3-cyclopentyloxy-4-methoxyphenylacetic acid (1.00 g) and 1,1'-carbonyldiimidazole (821 mg) in dichloromethane (5 ml) was stirred at room temperature, under argon, for 2 hours. The resulting solution was added to a stirred solution of 2-amino-6-nitrophenol (723 mg) in dichloromethane (10 ml) and the mixture stirred at room temperature, under argon, overnight. The reaction mixture was diluted with water (100 ml) and extracted with dichloromethane (3×50 ml). The combined organic extracts were washed with water (100 ml), 1N HCl (50 ml) and brine (50 ml), dried over CaSO$_4$ and evaporated in-vacuo to yield the title compound (1.05 g, 68%) as an orange solid. $\delta_H$ (250 MHz;$d_6$ DMSO), 1.58–1.97 (8H,m,4 ×CH$_2$), 3.73 (2H,s,CH$_2$), 3.87 (3H,s, OMe), 4.79 (1H,m,CH), 6.78–6.93 (3H,m,ArH), 6.98 (1H, t,ArH), 7.78 (1H,dd,ArH), 7.95 (1H,bs,CONH), 8.71 (1H, dd,ArH), 10.5 (1H,bs,ArOH).

(c) 2-(3-cyclopentyloxy-4-methoxybenzyl)-7-nitrobenzoxazole

A solution of N-(2-hydroxy-3-nitrophenyl)-3-cyclopentyloxy-4-methoxyphenylacetamide (2.0 g) and pyridinium p-toluene-sulphonate (500 mg) in xylene (140 ml) was refluxed, under nitrogen, overnight. The reaction mixture was cooled to room temperature, diluted with water (100 ml) and extracted with dichloromethane (3×75 ml). The combined organic extracts were washed with water (3×100 ml), brine (100 ml), dried (CaSO$_4$) and evaporated in-vacuo to yield an orange oil. The oil was purified by flash chromatography (SiO$_2$;dichloromethane;ethanol;ammonia (50:1:0.1)) to yield the title compound (1.107 g, 58%) as an orange solid (top 95°–98.5° C.). $\delta_H$ (250 MHz;$d_6$ DMSO) 1.45–1.95 (8H,m,4×CH$_2$), 3.70 (3H,s,OMe), 4.36 (2H, s,CH$_2$), 4.74 (1H,m,CH), 6.89 (2H,bs,ArH), 7.02 (1H,bs, ArH), 7.56 (1H,t,ArH), 8.15 (1H,dd,ArH), 8.17 (1H,dd, ArH). m/z 368 (M$^+$), 338 (M—NO), 300 (M—C$_5$H$_8$), 285, 270, 253, 149, 137, 123, 100.

EXAMPLE 7

2-(3-cyclopentyloxy-4-methoxybenzyl)-4-hydroxybenzoxazole (a) 2-aminoresorcinol A suspension of 2-nitroresorcinol (4.995 g) and platinum (IV) oxide (356 mg) in ethanol (90 ml) was hydrogenated, at room temperature, at 100 p.s.i. for 4 hours. The reaction mixture was filtered through celite, the filter cake washed with methanol (50 ml), and the combined filtrate evaporated in-vacuo to yield a brown solid. The solid was suspended in dichloromethane (100 ml) and evaporated to dryness to yield the title compound (3.83 g, 95%) as a brown solid. $\delta_H$ (250 Mhz; $d_6$ DMSO) 3.85 (2H,br s,NH$_2$), 6.20 (3H,m,ArH), 8.85 (2H,br s,ArOH).

(b) N-(2,6-dihydroxyphenyl)-3-cyclopentyloxy-4-methoxyphenylacetamide

A suspension of 3-cyclopentyloxy-4-methoxyphenylacetic acid (2.49 g) and 1,1'-carbonyldiimidazole (2.31 g) in dichloromethane (10 ml) was stirred at room temperature, under argon, for 2 hours. The resulting solution was added to a stirred suspension of 2-aminoresorcinol (1.62 g) in dichloromethane (15 ml) and the mixture stirred at room temperature, under argon, overnight. The reaction mixture was diluted with water (100 ml) and extracted with dichloromethane (3×50 ml). The combined organic extracts were washed with water (100 ml), 1N HCl (100 ml) and brine (100 ml), dried over CaSO$_4$ and evaporated in-vacuo to yield the title compound (2.122 g, 60%) as a beige solid. $\delta_H$ (250MHz;$d_6$DMSO) 1.53–1.95 (8H,m,4×CH$_2$), 3.65 (2H, s,CH$_2$), 3.70 (3H,s,OMe), 4.75 (1H,m, CH), 6.3 (1H,s,ArH), 6.35 (1H,s,ArH), 6.90 (4H,m, ArH), 9.40 (2H,s,ArOH), 9.6 (1H,s,CONH).

(c) 2-(3-cyclopentyloxy-4-methoxybenzyl)-4-hydroxybenzoxazole

A solution of N-(2,6-dihydroxyphenyl)-3-cyclopentyloxy-4-methoxyphenylacetamide (2.10 g) and pyridinium p-toluene-sulphonate (532 mg) in xylene (100 ml) was refluxed, under nitrogen, overnight. The reaction mixture was cooled to room temperature, diluted with water (100 ml), and extracted with dichloromethane (3×75 ml). The combined organic extracts were washed with water (3×100 ml), brine (100 ml), dried (CaSO$_4$) and evaporated in-vacuo to yield a pale brown solid. The solid was purified by flash chromatography (SiO$_2$; dichloromethane;methanol (50:1)) to yield the title compound (1.027 g, 51%) as a white solid (mp 172°–181° C.). $\delta_H$ (250MHz;$d_6$ DMSO) 1.53–1.85 (8H,m,4×CH$_2$), 3.70 (3H, s,OMe), 4.18 (2H,s, CH$_2$), 4.72 (1H,m,CH), 6.69 (1H,dd,ArH), 6.82 (1H,dd, ArH), 6.89 (1H,d,ArH), 6.93 (1H,d,ArH), 7.02 (1H,dd, ArH), 7.11 (1H,t,ArH), 10.22 (1H,s,ArOH). m/z 339 (M$^+$), 271 (M—C$_5$H$_8$), 256,242,228,199,149,137,123,94.

EXAMPLE 8

4-acetoxy-2-(3-cyclopentyloxy-4-methoxybenzyl)benzoxazole (a) 4-acetoxy-2-(3-cyclopentyloxy-4-methoxybenzyl)benzoxazole A solution of 2-(3-cyclopentyloxy-4-methoxybenzyl)-4-hydroxybenzoxazole (200 mg) and acetyl chloride (84 μl) in pyridine (6 ml) was stirred at room temperature, under nitrogen, for 3 hours. The reaction mixture was diluted with methanol (20 ml) and evaporated in-vacuo to yield a yellow solid. The solid was purified by flash chromatography (SiO$_2$; dichloromethane; methanol (50:1)) and crystallized from ether/petroleum ether to yield the title compound (119 mg, 53%) as a white crystalline solid (mp 65–°67° C.). $\delta_H$ (250MHZ;d$_6$ DMSO) 1.45–1.92 (8H,m,4×CH$_2$), 2.35 (3H, s,MeC(O)), 3.70 (3H,s,OMe), 4.24 (2H,s,CH$_2$), 4.73 (1H, m,CH), 6.82 (1H,dd,ArH), 6.89 (1H,d,ArH), 6.95 (1H,d, ArH), 7.12 (1H,dd,ArH), 7.36 (1H,t,ArH), 7.58 (1H,dd, ArH).

Rf (SiO$_2$;dichloromethane;methanol (50:1)) 0.63

EXAMPLE 9

Protocols for PDE IV, PDE III, and PDE V inhibition activity are set forth below:

Type III Phosphodiesterase Enzyme Isolation Protocol

The Type III PDE is isolated from human platelets using a procedure similar to that previously described by Weishaar, R. E. et al., Biochem. Pharmacol., 35:787, 1986. Briefly, 1–2 units of platelets are suspended in an equal volume of buffer (20 mM Tris-HCl, pH 7.5, containing 2 mM magnesium acetate, 1 mM dithiothreitol, and 5 mM Na$_2$ EDTA). The proteinase inhibitor phenylmethyl-sulfonyl fluoride (PMSF) is also included in this buffer at a final concentration of 200 μM. The suspension is homogenized using a polytron and the homogenate centrifuged at 100, 000×g for 60 minutes. This and all subsequent procedures are performed at 0°–4° C. The supernatant is then filtered through four layers of gauze and applied to a DEAE-Trisacryl M column, previously equilibrated with buffer B (20 mM Tris-HCl, pH 7.5, containing 1 mM magnesium acetate, 1 mM dithiothreitol and 200 μM PMSF). After application of the sample, the column is washed with several bed volumes of buffer B, after which the different forms of PDE are eluted from the column using two successive linear NaCl gradients (0.05–0.15M, 300 ml total; 0.15–0.40M, 200 ml total). Five ml fractions are collected and assayed for cyclic AMP and cyclic GMP PDE activity. Fractions containing PDE III activity are pooled and dialyzed overnight against 4 L of buffer B. The dialyzed PDE III is then concentrated to 10% of the original volume, diluted to 50% with ethylene glycol monoethyl ether and stored at –20° C. PDE III can typically be retained for up to four weeks with little or no loss of activity.

Measuring Type III PDE Activity

Enzyme activity is assessed by measuring the hydrolysis of [$^3$H]-cyclic AMP, as described by Thompson, W. J. et al., Adv. Cyclic Nucleotide Res. 10:69, 1979. The cyclic AMP concentration used in this assay is 0.2 μM, which approximates to the K$_m$ value. Protein concentration is adjusted to ensure that no more than 15% of the available substrate is hydrolyzed during the incubation period.

All test compounds are dissolved in dimethyl sulfoxide (final concentration of 2.5%). This concentration of dimethyl sulfoxide inhibits enzyme activity by approximately 10%.

Type IV Phosphodiesterase Enzyme Isolation Protocol

The Type IV PDE is isolated from bovine tracheal smooth muscle using a procedure similar to that previously described by Silver, P. J. et al., Eur. J. Pharmacol. 150:85, 1988.(1). Briefly, smooth muscle from bovine trachea is minced and homogenized using a polytron in 10 volumes of an extraction buffer containing 10 mM Tris-acetate (pH 7.5), 2 mM magnesium chloride, 1 mM dithiothreitol and 2,000 units/ml of aprotinin. This and all subsequent procedures are performed at 0°–4° C. The homogenate is sonicated and then centrifuged at 48,000×g for 30 minutes. The resulting supernatant is applied to a DEAE Trisacryl M column previously equilibrated with sodium acetate and dithiothreitol. After applications of the sample, the column is washed with sodium acetate/dithiothreitol, after which the different forms of PDE are eluted from the column using a linear Tris-HCl NaCl gradient. Fractions containing Type IV PDE are collected, dialyzed and concentrated to 14% of the original volume. The concentrated fractions are diluted to 50% with ethylene glycol and stored at –20° C.

Measuring Type IV PDE Activity

Enzyme activity is assessed by measuring the hydrolysis of [$^3$H]-cyclic AMP, as described by Thompson, W. J. et al., Adv. Cyclic Nucleotide Res. 10:69, 1979. The cyclic AMP concentration used in this assay is 0.2 μM, which approximates the K$_m$ value. Protein concentration is adjusted to ensure that no more than 15% of the available substrate is hydrolyzed during the incubation period.

All test compounds are dissolved in dimethyl sulfoxide (final concentration of 2.5%). This concentration of dimethyl sulfoxide inhibits enzyme activity by approximately 10%.

EXAMPLE 10

Following the above procedures, the PDE III, PDE IV inhibition for the compounds of Examples 1–8, and rolipram are tested and compared. The results are shown in Tables 1–2 below:

TABLE 1

PDE III ACTIVITY

| Compound | % Inhibition | | | |
|---|---|---|---|---|
| | 1.0 μM | 10 μM | 100 μM | |
| Ex. 1 | 5 | 22 | precipitate | |
| Ex. 2 | 0 | 13 | precipitate | |
| Ex. 3 | 2 | 2 | precipitate | |
| Ex. 4 | 16 | 55 | precipitate | |
| Ex. 5 | 4 | 50 | precipitate | |
| Ex. 6 | 58 | 93 | precipitate | |
| Ex. 7 | 6 | 27 | precipitate | |
| Ex. 8 | 5 | 8 | 43 | |
| Rolipram | — | 7 | 18 | 35 |

TABLE 2

PDE IV ACTIVITY

| Compound | % Inhibition | | | |
|---|---|---|---|---|
| | 0.1 μM | 1.0 μM | 10 μM | 100 μM |
| Ex. 1 | 53 | 82 | 92 | |
| Ex. 2 | 83 | 87 | precipitate | |
| Ex. 3 | 84 | 87 | precipitate | |
| Ex. 4 | 1 | 36 | 46 | |
| Ex. 5 | 8 | 36 | 77 | 82 |
| Ex. 6 | 10 | 41 | 85 | 96 |

TABLE 2-continued

PDE IV ACTIVITY

| Compound | % Inhibition | | | |
|---|---|---|---|---|
| | 0.1 µM | 1.0 µM | 10 µM | 100 µM |
| Ex. 7 | 21 | 63 | 93 | 104 |
| Ex. 8 | 21 | 56 | 94 | 102 |
| Rolipram | | 36 | 67 | |

While the invention has been illustrated with respect to the production and use of a particular compound, it is apparent that variations and modifications of the invention can be made without departing from the spirit or scope of the invention.

What is claimed is:

1. A compound of the formula:

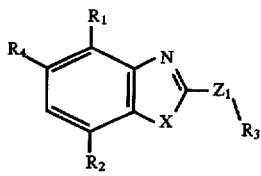

wherein:

X is O or S;

$R_1$ is selected from the group consisting of hydrogen, halogen, hydroxy, nitro, $QZ_2$, $OQZ_2$, $OCOQZ_2$, $NHQZ_2$ and $NCOQZ_2$;

$R_2$ is selected from the group consisting of halogen, hydroxy, nitro, $QZ_2$, $OQZ_2$, $OCOQZ_2$, $NHQZ_2$ and $NCOQZ_2$ wherein:

Q is a straight-chain or branched alkylene, alkenylene or alkynylene group having from 1 to 12 carbon atoms;

$Z_2$ is pyridyl optionally substituted with one to three groups selected from halogen atoms, $C_1-C_6$ alkyl groups, OH, OQH, $NO_2$, $NH_2$, $CO_2QH$, $CON(QH)_2$, OCOQH, and $OCON(QH)_2$;

wherein at least one of $R_1$ or $R_2$ has a substituent with $Z_2$;

$R_3$ is a six membered carbocyclic aryl substituted with 1-3 members of the group consisting of OH, O—($C_1-C_6$) alkyl, O(CO)($C_1-C_6$) alkyl, O—($C_3-C_{10}$) cycloalkyl, $R_5$ or $R_6$;

$Z_1$ is a linkage selected from the group consisting of —$CH_2$—, —$CH_2CH_2$—, —$CH(CH_3)$— and —$C(CH_3)_2$—;

$R_4$ is hydrogen or a halogen;

$R_5$ is hydrogen or $C_1-C_{12}$ alkyl; and $R_6$ is $C_1-C_4$ alkyl.

2. A compound according to claim 1 wherein one of $R_1$ is hydrogen; X is O and $R_4$ is halogen.

3. A compound according to claim 1, wherein $Z_1$ is selected from the group consisting of —$CH_2$—, and —$CH_2CH_2$—.

4. A compound according to claim 3 wherein $R_4$ is chlorine.

5. A compound according to claim 1 wherein Q is an alkenylene.

6. A compound according to claim 1 wherein Q is an alkynylene.

7. A compound according to claim 1, wherein Q is an alkynylene and $Z_2$ is a pyridine.

8. A compound according to claim 1, wherein $R_3$ is a substituted phenyl.

9. A compound according to claim 8, wherein said phenyl is selected from the group consisting of chlorophenyls, fluorophenyls and chloro-fluorophenyls.

10. A compound according to claim 8, wherein $R_3$ is 3-cyclopentyloxy-4-methoxyphenyl or 3,4-dimethoxyphenyl.

11. A compound according to claim 8, wherein $R_3$ is selected from the group consisting of 3,5-di-t-butyl-4-hydroxyphenyl; and 3,5-di-t-butyl-4-acetyloxyphenyl.

12. A compound according to claim 1, wherein said alkenylene is —CH=CH—, —$CH_2$—CH=CH— or —CH=CH—$CH_2$—.

13. A compound according to claim 1, wherein said alkynylene is —C≡C— or —C≡C—$CH_2$—.

14. A compound according to claim 1, wherein Q is an alkylene group.

15. A compound according to claim 14, wherein said alkylene is —$CH_2$—, —$CH_2$—$CH_2$— or —$CH_2$—$CH_2$—$CH_2$—.

16. A compound according to claim 1, wherein $R_5$ is a branched or straight chain alkyl group of 1–12 carbon atoms.

17. A compound according to claim 16, wherein $R_5$ is methyl or ethyl.

18. A compound according to claim 1, wherein $R_6$ is an alkyl group of 1–4 carbon atoms.

19. A compound according to claim 1 of the formula: 5-chloro-2-(3,5-di-t-butyl-4-hydroxy-benzyl)-7-(2-(2-pyridyl)-ethynyl)-benzoxazole.

20. A pharmaceutical composition comprising a compound having the chemical structure set forth in claim 1.

21. The pharmaceutical composition of claim 20, wherein said compound is selected from the group consisting of:

5-chloro-2-(3,5-di-t-butyl-4-hydroxy-benzyl)-7-(2-(2-pyridyl)-ethynyl)- benzoxazole;

7-bromo-5-chloro-2-(3,4-dimethoxy-benzyl)-benzoxazole; and 2-(3-cyclopentyloxy-4-methoxy-benzyl)-7-nitro-benzoxazole.

22. A method of treating a mammal suffering from a disease state selected from the group consisting of asthma, allergies, inflammation, depression, dementia, atopic diseases, rhinitis comprising administering a therapeutically effective amount of compound according to claim 1.

23. The method of claim 22, wherein the composition is selected from the group consisting of:

2-(3-cyclopentyloxy-4-methoxybenzyl)-5-chloro-7-allylbenzoxazole;

5-chloro-2-(3,5-di-t-butyl-4-hydroxy-benzyl)-7-(2-(2-pyridyl)-ethynyl)-benzoxazole;

7-bromo-5-chloro-2-(3,4-dimethoxy-benzyl)-benzoxazole;

2-(3-cyclopentyloxy-4-methoxy-benzyl)-7-nitro-benzoxazole;

2-(3-cyclopentyloxy-4-methoxy-benzyl)-4-hydroxy-benzoxazole;

4-acetoxy-2-(3-cyclopentyloxy-4-methoxy-benzyl) benzoxazole; and 7-bromo-5-chloro-2-(3-cylopentyloxy-4-methoxybenzyl)-benzoxazole.

24. The method of claim 23 wherein the composition is 5-chloro-2-(3,5-di-t-butyl-4-hydroxy-benzyl)-7-(2-(2-pyridyl)-ethynyl)-benzoxazole.

* * * * *

UNITED STATES PATENT AND TRADEMARK OFFICE
CERTIFICATE OF CORRECTION

PATENT NO. : 5,665,737
DATED : September 9, 1997
INVENTOR(S) : David John Cavalla, et. al.

It is certified that error appears in the above-identified patent and that said Letters Patent is hereby corrected as shown below:

Title page, item [75], inventors: "John David Cavalla" should read-- David John Cavalla--.

Signed and Sealed this

Sixth Day of February, 2001

Attest:

Attesting Officer

Q. TODD DICKINSON
Director of Patents and Trademarks

REEXAMINATION CERTIFICATE (3736th)
United States Patent [19]
Cavalla et al.

[11] B1 5,665,737
[45] Certificate Issued Feb. 16, 1999

[54] SUBSTITUTED BENZOXAZOLES

[75] Inventors: John David Cavalla, Cambridge, England; Lloyd J. Dolby, Eugene, Oreg.; Peter Hofer, Liestal, Switzerland; Mark Chasin, Manalapan, N.J.

[73] Assignee: Euro-Celtique, S.A., Luxembourg, Luxembourg

Reexamination Request:
No. 90/004,882, Jan. 5, 1998

Reexamination Certificate for:
Patent No.: 5,665,737
Issued: Sep. 9, 1997
Appl. No.: 321,730
Filed: Oct. 12, 1994

[51] Int. Cl.$^6$ ...................... A61K 31/42
[52] U.S. Cl. .............. 514/338; 514/365; 514/367; 514/375; 548/179; 548/217; 548/205; 546/270.1; 546/271.7
[58] Field of Search .............. 514/338; 546/270.1, 546/271.7

[56] References Cited

U.S. PATENT DOCUMENTS

| | | | |
|---|---|---|---|
| 2,320,654 | 6/1943 | Riester . | |
| 3,262,929 | 7/1966 | Okubo | 548/217 |
| 3,491,106 | 1/1970 | Freyermuth et al. | 548/179 |
| 3,586,670 | 6/1971 | Brenneisen et al. | 548/217 |
| 3,647,812 | 3/1972 | Smith | 548/179 |
| 3,666,769 | 5/1972 | Jones et al. | 548/179 |
| 3,669,979 | 6/1972 | Freyermuth | 548/179 |
| 3,962,452 | 6/1976 | Evans et al. | 514/375 |
| 5,047,411 | 9/1991 | Takasugi | 514/338 |
| 5,622,977 | 4/1997 | Warrellow et al. | 514/336 |
| 5,633,257 | 5/1997 | Warrellow et al. | 514/277 |

FOREIGN PATENT DOCUMENTS

| | | |
|---|---|---|
| 0 332988 | 9/1989 | European Pat. Off. . |
| 2 008464 | 9/1970 | Germany . |
| 2 314676 | 10/1973 | Germany . |
| 2 346034 | 4/1974 | Germany . |
| 57-021375 | 2/1982 | Japan . |
| 57-21375 | 2/1982 | Japan . |
| 8-113567 | 7/1996 | Japan . |
| 1 260793 | 1/1972 | United Kingdom . |
| 94-10118 | 5/1994 | WIPO . |
| WO 9508534 | 3/1995 | WIPO . |
| WO 9517392 | 6/1995 | WIPO ............ C07D 261/12 |
| WO 9517399 | 6/1995 | WIPO . |

OTHER PUBLICATIONS

Chem. Abs. 117:212391m (1992).
Chem. Abs. 119:245336t (1993).
Chem. Abs. 121:57373v (1994).
Chem. Abs. 121:134105p (1994).
Chem. Abs. 124:86997u (1995).
Chem. Abs. 124:176077y (1994).
Annual Drug Report, p. 637—KB—2683 (1991).

*Primary Examiner*—Donald G. Daus

[57] ABSTRACT

Novel compounds which are effective PDE IV inhibitors are disclosed. The compounds possess improved PDE IV inhibition as compared to theophylline or rolipram, with improved selectivity with regard to, e.g., PDE III inhibition.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–20, and 22 is confirmed.

Claim 23 is cancelled.

Claims 21 and 24 are determined to be patentable as amended.

21. The pharmaceutical composition of claim 20 wherein said compound is [selected from the group consisting of:] 5-chloro-2-(3,5-di-t-butyl-4-hydroxy-benzyl)-7-(2-(2-pyridyl)-ethynyl)-benzoxazole[; 7-bromo-5-chloro-2-(3,4-dimethoxy-benzyl) benzoxazole; and 2-(3-cyclopentyloxy-4-methoxy-benzyl)-7-nitro-benzoxazole].

* * * * *